United States Patent [19]
Rodriguez

[11] Patent Number: 5,821,424
[45] Date of Patent: Oct. 13, 1998

[54] METHOD AND APPARATUS FOR ANALYZING THE FILL CHARACTERISTICS OF A PACKAGING CONTAINER

[75] Inventor: Julio G. Rodriguez, Idaho Falls, Id.

[73] Assignee: Lockheed Idaho Technologies Company, Idaho Falls, Id.

[21] Appl. No.: 543,719

[22] Filed: Oct. 16, 1995

[51] Int. Cl.$^6$ .................................................. G01B 9/02
[52] U.S. Cl. .................................................. 73/657; 73/52
[58] Field of Search .................. 73/656, 657, 655, 73/579, 290 V, 54.41, 52, 61.49, 61.79, 64.53; 364/507, 508; 356/35.5, 428, 488; 367/93, 94

[56] References Cited

U.S. PATENT DOCUMENTS

| | | | |
|---|---|---|---|
| 3,792,606 | 2/1974 | Munger | 73/40 |
| 3,877,295 | 4/1975 | Hartman | 73/595 |
| 4,179,937 | 12/1979 | Koblanski | 73/646 |
| 4,406,157 | 9/1983 | Miyahara et al. | 73/52 |
| 4,659,224 | 4/1987 | Monchalin | 73/657 |
| 5,056,357 | 10/1991 | Dymling | 73/54.41 |
| 5,070,724 | 12/1991 | Wubs et al. | 73/45.5 |
| 5,099,848 | 3/1992 | Parker | 73/575 |
| 5,131,748 | 7/1992 | Monchalin | 73/657 |
| 5,146,289 | 9/1992 | Newman | 73/656 |
| 5,408,305 | 4/1995 | Webster | 356/35.5 |
| 5,505,090 | 4/1996 | Webster | 73/657 |

OTHER PUBLICATIONS

*Dantec Technical News*, (May 1988) by Dantec Electronics Inc.
*41 X 62 Compact Laser Vibrometer—manual*, pp. 13–14, Ch. 5 (Sep. 1991) produced by Dantec Electronics Inc.
SAS/STAT User's Guide Version 6, 4th ed., vol. 1., Ch. 20, pp. 678–685. SAS Institute, Inc., Cary, NC (USA), 4$^{th}$ Ed.1989 (no month), 3$^{rd}$ printing Jun. 1993.

*Primary Examiner*—Christine K. Oda
*Attorney, Agent, or Firm*—Klaas Law O'Meara & Malkin

[57] ABSTRACT

A system for analyzing the fill characteristics of a container. A container having a filling material therein is positioned adjacent a sound generator. Sound waves from the generator are applied to the container, causing it to vibrate. A vibration detector is used to determine the amount of container vibration. A preferred vibration detector involves a laser vibrometer which applies a reference laser beam to the vibrating container. The reference beam is reflected off of the container to generate a reflected laser beam. The reflected beam experiences a Doppler frequency shift compared with the reference beam which is caused by container vibration. The Doppler shift of the reflected beam is then compared with standardized Doppler shift data from a control container. Repeated Doppler shift measurements may also be undertaken which are converted into a vibration profile that is compared with a standardized vibration profile from a control container.

1 Claim, 4 Drawing Sheets

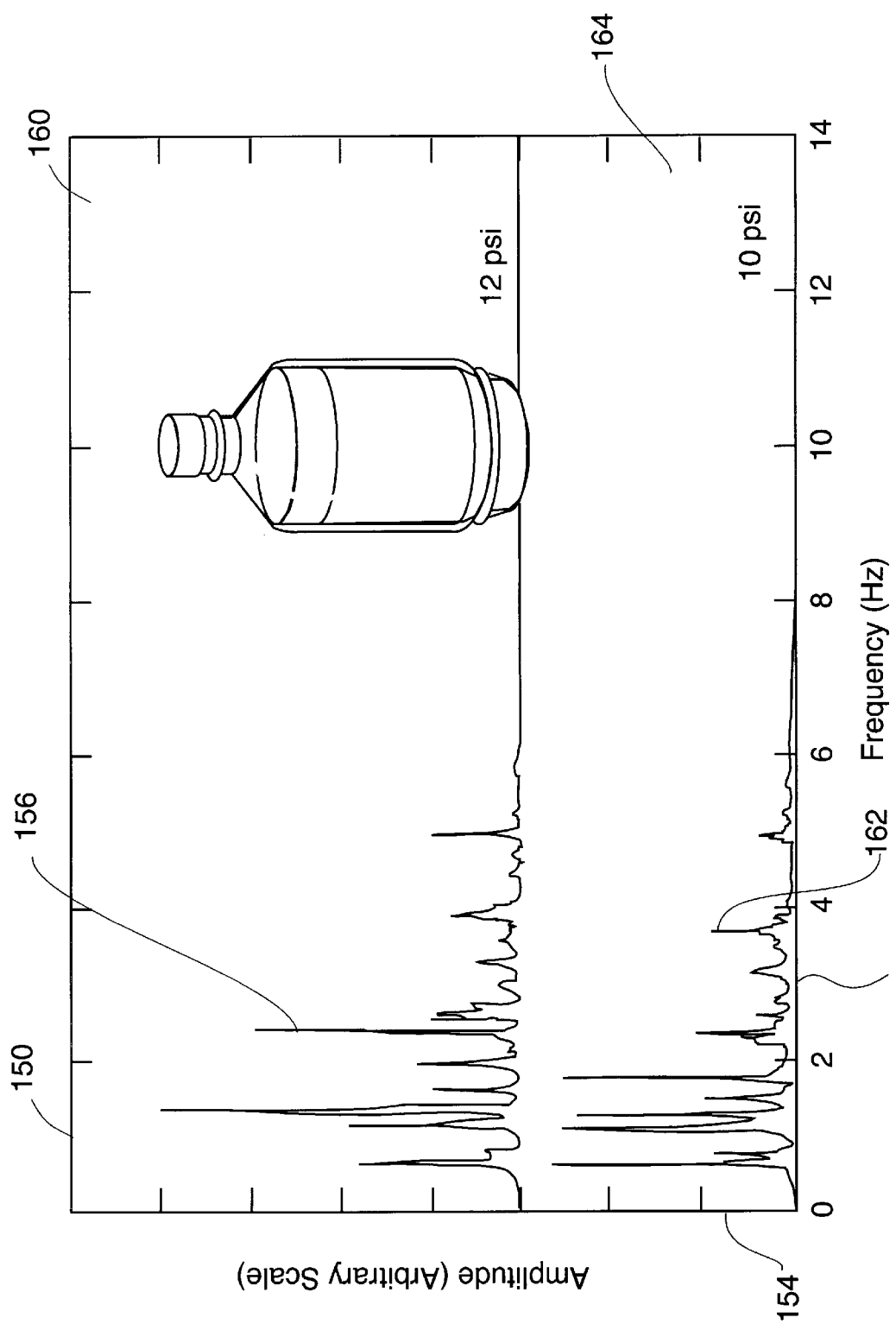

METHOD AND APPARATUS FOR ANALYZING THE FILL CHARACTERISTICS OF A PACKAGING CONTAINER

CONTRACTUAL ORIGIN OF THE INVENTION

The United States has rights in this invention pursuant to contract number DE-AC07-76ID01570 between the U.S. Department of Energy and EG&G Idaho, Inc., now contract number DE-AC07-94ID13223 between the U.S. Department of Energy and Lockheed Idaho Technologies Company.

BACKGROUND OF THE INVENTION

The present invention generally relates to the testing of containers, and more particularly to the non-intrusive analysis of packaging containers and their contents using a sound wave (acoustic excitation) system.

In recent years, many developments have been made in the field of mass production packaging technology. These developments have created a corresponding need for rapid and accurate container testing methods. To achieve a maximum level of quality control (which is especially important in the food processing industry), the containers of interest must be tested to determine if they are properly filled with the desired amount of materials, and whether they have the necessary level of structural integrity (e.g. are properly sealed). It is especially important to be certain that vacuum-packed food products are properly manufactured to avoid the introduction of air or other contaminants. In packages which contain perishable food items, the presence of air can cause bacterial spoilage and other health concerns. It is therefore necessary in a variety of different industries to test containers for proper fill characteristics. The term "fill characteristics" as used herein shall generally involve the internal environment and contents of the test container, as well as the amount of materials within the container including undesired compositions (e.g. air and/or water which enter because of container leakage).

It is likewise preferred that packaging containers be tested in a manner which is minimally intrusive. Intrusive testing methods involve procedures in which the test container is physically handled, manipulated, placed in contact with solid objects (e.g. striking members), and/or opened to examine its contents and internal environment. For example, U.S. Pat. No. 5,070,724 discloses a method for testing a "casing" material in which the casing is supplied with a gas and placed in a container filled with liquid. Any gas bubbles which escape from the casing (due to leaks) come in contact with the container walls and cause vibrations which are thereafter detected. U.S. Pat. No. 3,877,295 involves a method for testing bottles in which a test bottle is initially struck by an impact mechanism. The resulting sound waves generated from this process are thereafter detected and analyzed to determine the structural characteristics of the bottle. U.S. Pat. No. 3,792,606 describes a method for detecting leaks in a container. Specifically, a pressurized fluid (e.g. air) is initially applied to the test object. A detection system consisting of a microphone is positioned adjacent the object in order to detect high frequency sound vibrations caused by passage of the pressurized fluid through openings (e.g. leaks) in the object.

Intrusive testing methods traditionally involve increased time, effort, and expense. Specifically, intrusive testing processes generally reduce the overall efficiency of the entire quality control program under consideration. In addition, destructive testing methods in which the test containers are opened or otherwise damaged typically require disposal of the containers. As a result, substantial amounts of waste products are generated.

A need therefore remains for a container testing system which is entirely non-intrusive (e.g. does not involve any physical contact, handling, manipulation, and/or opening of the test container during analysis). The present invention satisfies this need by providing a unique testing method which uses sound and light in a non-intrusive manner to test containers with a high degree of efficiency. As a result, a variety of different containers can be analyzed in an accurate, inexpensive, and effective manner which is well-suited to mass production manufacturing processes. Accordingly, the present invention represents a significant advance in the field of packaging technology as discussed below.

SUMMARY OF THE INVENTION

It is an object of the present invention to provide an efficient testing system for analyzing the fill characteristics of a packaging container.

It is another object of the invention to provide a container testing system which is non-intrusive (e.g. does not involve the physical contact, handling, manipulation, and/or opening of the test containers during analysis).

It is another object of the invention to provide a container testing system which avoids the use of complex and elaborate testing machinery.

It is another object of the invention to provide a container testing system which is applicable to a wide variety of packaging materials manufactured from many different compositions including but not limited to metal, glass, plastic or paper.

It is a further object of the invention to provide a container testing system that is capable of analyzing many different container types in a minimal amount of time which is useful in mass production manufacturing processes.

It is still further object of the invention to provide a container testing system which avoids the generation of waste materials which normally result when destructive testing methods are employed.

It is a still further object of the invention to provide a container testing system which enables testing to occur without physically touching the container during analysis.

It is an even further object of the invention to provide a container testing system in which the above-listed goals are accomplished through the use of sound and laser light in a unique manner to obtain a data profile which clearly and accurately characterizes the containers being tested.

In accordance with the foregoing objects, the present invention involves a highly efficient, non-intrusive system for determining the fill characteristics of a container having a selected filling material therein. Data associated with the test container may then be compared with standardized data corresponding to a reference (control) container having known fill characteristics. It can then be determined whether the test container has the correct filling material therein, the proper amount of filling material, and/or the desired internal environment (e.g. a vacuum) as discussed further below. Further advantages of the claimed invention will become readily apparent from the following summary which involves a general overview of the invention. Specific details and features of the invention will be set forth in the Detailed Description of Preferred Embodiments provided below.

To begin the testing process, a test container having a filling material therein is initially provided. Many different containers produced from a variety of compositions may be analyzed in accordance with the invention. For example, containers manufactured from metal, glass, paper, or plastic can be analyzed with a high degree of effectiveness. Likewise, containers of many different sizes, shapes, and uses may be tested. While food packaging containers are of primary importance in the claimed invention, other container units may also be analyzed ranging from medicine packaging materials to explosive-containing military components is (e.g. shells). Accordingly, the present invention shall not be limited regarding the type, size, and construction materials associated with the test containers.

An inspection system is then provided which consists of numerous components. The system first includes sound generating means for producing sound waves. As discussed below, the sound generating means is used to generate and deliver sound waves to the test container which causes the container to vibrate. In a preferred embodiment, the sound generating means will include audio signal production means for producing an initial audio signal, and amplifier means connected to the audio signal production means for generating an amplified audio signal from the initial audio signal. Also included is at least one speaker unit operatively connected to the amplifier means for receiving the amplified audio signal and producing sound waves which are applied to the container in accordance with the method of the present invention.

Next, vibration sensing means is provided which is used to detect container vibration during the application of sound waves to the container. As discussed below, the fill characteristics (e.g. a fill profile or "signature") of the test container may be obtained by determining the vibration characteristics of the container which are then compared to standardized data for a reference (control) container having known fill characteristics. To accomplish this goal, the vibration sensing means includes laser light delivery means for applying a reference beam of laser light to the container during the application of sound waves to the container by the sound generating means. The reference beam comes in contact with the container and is thereafter reflected off of the container in order to generate a reflected beam of laser light. The reflected beam experiences a Doppler shift in frequency compared with the frequency of the reference beam, with the Doppler shift being caused by vibration of the container.

The vibration sensing means further includes frequency shift detector means for measuring the Doppler shift associated with the reflected beam of laser light so that a comparison with the standardized data from the reference container can be made. In a preferred embodiment as described herein, a representative vibration sensing means which includes all of the components listed above will consist of a commercially-available laser vibrometer as described in detail below.

After providing the test container, the sound generating means, and the vibration sensing means as described above, the process of the present invention is initiated by positioning the speaker unit of the sound generating means adjacent the container. In a preferred embodiment, the speaker unit will be positioned about 2–4 inches from the container. However, the present invention shall not be limited to this numerical range or any of the other numerical values expressed herein which are provided for example purposes. Specific numerical parameters for a particular test procedure will vary in view of the container and filling materials being analyzed, and will be determined in accordance with routine pilot studies on the materials of interest.

Thereafter, the sound generating means is activated in order to apply sound waves to the container from the speaker unit. In an optimum and preferred embodiment suitable for the purposes expressed herein, the sound waves will be applied over a time period of about 0.01–10 seconds at a frequency of about 100–5000 Hz and a volume level of about 70–80 decibels. However, these parameters may again be varied as discussed above. The delivery of sound waves from the sound generating means to the container will cause the container to vibrate in a unique manner which depends on the particular container being tested and its fill characteristics (e.g. the type and amount of filling materials therein, as well as the presence or absence of air in the container). As a result, a unique vibration signature or profile may be obtained for the test container which can then be compared to the vibration profile of a reference container as described in greater detail below.

To determine the amount of vibration experienced by the test container (e.g. the frequency and amplitude of the vibration), the vibration sensing means is used to apply the reference beam of laser light to the container during the application of sound waves as previously described. In a preferred embodiment, the reference beam is applied to the container at a power level of about 0.5–5 mW using a beam diameter of about 0.4–5 mm, with the specific values within these ranges being determined by preliminary testing. The reference beam comes in contact with the container and is thereafter reflected off of the container to generate a reflected beam of laser light. As previously stated, the reflected beam undergoes a Doppler shift in frequency compared with the reference beam, with the Doppler shift being caused by vibration of the container. The amount of Doppler shift will depend on the extent of container vibration which, in turn, depends on the test container and its fill characteristics.

Next, the Doppler shift associated with the reflected beam is measured using the frequency shift detector means. The resulting data may then be compared with previously-determined Doppler shift data obtained from a reference container having known (e.g. desired) fill characteristics. Any differences in the vibration profiles of the test container and the reference container will indicate that the test container deviates in some manner from the desired fill characteristics associated with the production process of interest. The test container can then be physically (manually) inspected to determine if it has the wrong filling materials therein, the incorrect amount of filling materials, and/or the presence of leaks. As stated above, any of these characteristics will produce variances in container vibration which may be determined as described above. The resulting information obtained from the claimed process can be used as part of a highly accurate quality control program in many different fields including the food processing industry.

To further enhance the accuracy of the claimed testing system, measurement of the Doppler shift associated with the reflected beam may be undertaken numerous times during the application of sound waves to the container in order to produce a set of data values. In an exemplary and preferred embodiment, measurement of the Doppler frequency shift will occur about 2–100 times during the application of sound waves to the test container. Using data processing means connected to the vibration sensing means (discussed in further detail below), an averaged vibration profile (also known as a vibration "spectra" or "signature") can be generated from the multiple data values. As previously indicated, the vibration signature of the test container will be based on the Doppler shift of the reflected beam which, in turn, will again depend on the container and its fill characteristics. The averaged vibration profile of the test container can then be compared with a previously-determined averaged vibration profile generated in the same manner which is associated with a reference (control) container having known fill characteristics. The resulting information can be used as part of a quality control program in many different fields as previously stated.

The present invention represents a significant advance in the field of analytical technology. Specifically, the claimed system for analyzing the fill characteristics of a container provides many benefits including (1) the ability to test containers in a non-destructive, non-intrusive manner which is highly accurate and economically efficient; (2) the capability of the present invention to accomplish container testing in a rapid manner using a minimal amount of equipment; and (3) the provision of a testing system which is suitable for both mass production manufacturing processes and the on-demand testing of individual samples. These and other objects, features, and advantages of the present invention shall be described below in the following Brief Description of the Drawings and Detailed Description of Preferred Embodiments.

BRIEF DESCRIPTION OF THE DRAWINGS

FIG. 4 is a comparative vibration profile of a representative test container (e.g. a plastic bottle) produced in accordance with a third Example.

DETAILED DESCRIPTION OF PREFERRED EMBODIMENTS

The present invention involves a unique and highly-efficient method for analyzing the fill characteristics of a container. As stated above, the term "fill characteristics" shall collectively involve the internal environment and contents of the container, as well as the amount of materials within the container including undesired compositions (e.g. air and water which enter because of container leakage). In particular, the fill characteristics of a selected container will encompass the type and quantity of materials inside the container and/or the structural integrity of the container. The present invention enables a test container to be characterized in a manner which allows comparison of the test container with a reference container having known fill characteristics. The term "reference container" as used herein shall involve a control container having specific and desired fill characteristics. In accordance with the invention, it can be determined with a high degree of accuracy whether the test container deviates from the reference container for any reason, including leakage of the test container or an improper amount of filling material inside the container. This type of system can be used as part of a mass production quality control program in the manufacture of packaged items. Testing is accomplished rapidly and efficiently in a non-intrusive manner. The term "non-intrusive" as used herein shall again involve a testing program which avoids the manipulation, handling, deformation, or opening of the test container during analysis. As a result, the claimed method avoids the time delays and/or generation of waste materials which occurs when destructive testing methods are employed.

While the present invention shall be described with primary reference to the testing of food package containers, it is prospectively applicable to many different technical fields and container types. For example, the invention may be used in a military environment to test sealed munitions for explosive quantity and fill characteristics. The claimed method is especially useful for this purpose since it is non-intrusive and does not involve handling, manipulation, and/or physical disruption (opening) of the container during testing. Accordingly, the present invention shall not be limited to the testing of any particular type of container.

Figure 1:
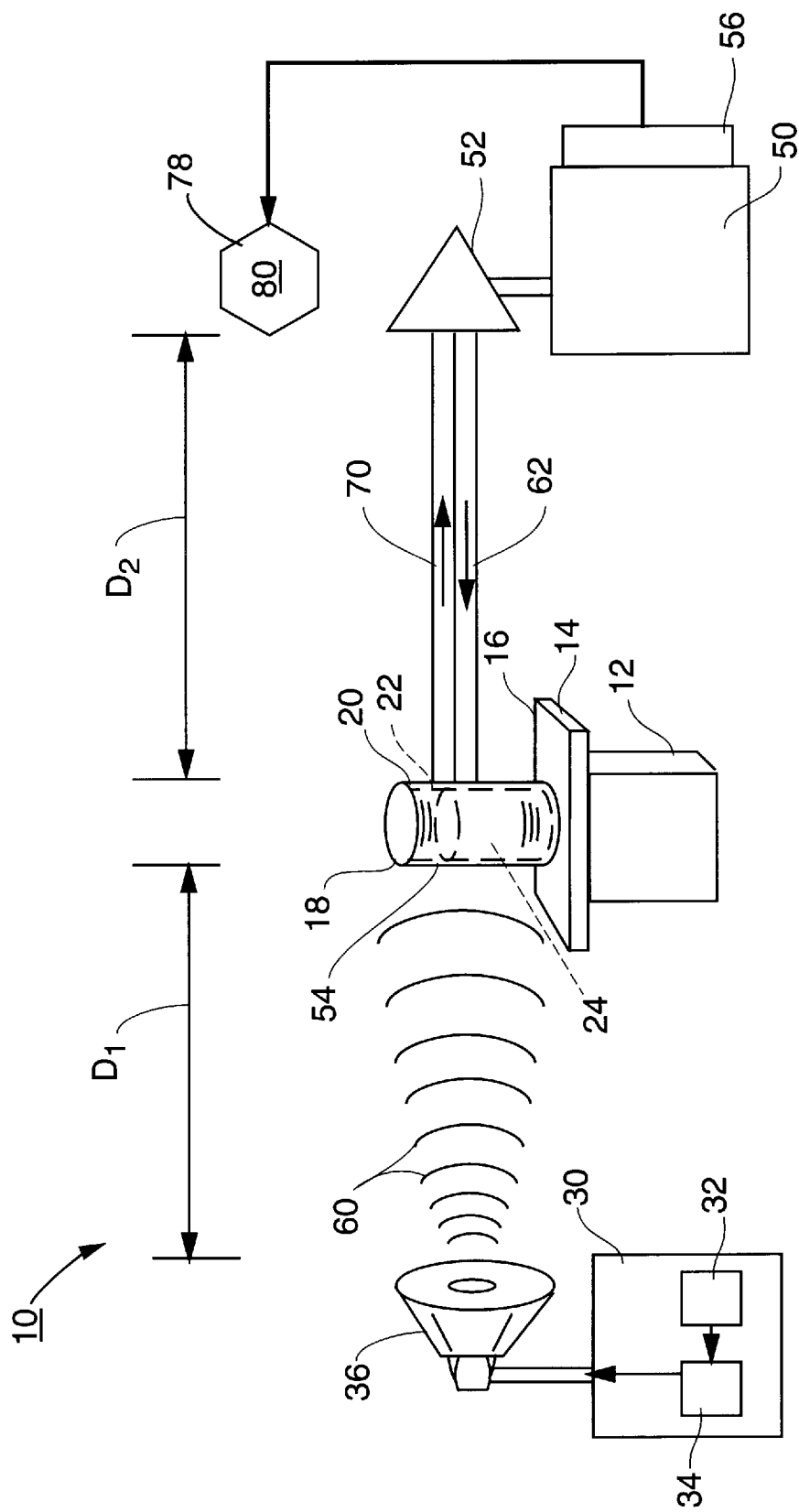
FIG. 1 is a schematic representation of an exemplary system suitable for testing a container in accordance with the method of the present invention.

With reference to FIG. 1, a schematic representation of a testing system used to analyze a test container in accordance with the invention is illustrated at reference number 10. The testing system 10 includes a variety of components which will now be described, followed by a discussion of the operational characteristics of the system 10. As illustrated in FIG. 1, system 10 first includes a support structure 12 on which the selected container is placed during a test procedure. In the embodiment of FIG. 1, the support structure 12 includes a planar, horizontally-positioned platform member 14 which is sized to receive the container thereon. The specific configuration and size of the support structure 12, as well as the platform member 14 will vary in view of the particular container being tested. In this regard, the present invention shall not be limited to any particular design, shape, or size in connection with the support structure 12. Likewise, the support structure 12 and platform member 14 may be manufactured from many different construction materials, including but not limited to metals, glass, plastics, and ceramic compositions. These materials are preferably used in amounts which (depending on the container being tested) produce a support structure 12 that is sufficiently heavy to prevent extraneous vibration of the structure 12 during a testing procedure. By using a support structure 12 which is sufficiently large and/or heavy to avoid extraneous vibration of the structure 12 during operation of the system 10, all of the vibrational activity will be restricted to the test container. In this manner, a maximum degree of accuracy and sensitivity will be achieved. The particular size, weight, and materials associated with the support structure 12 in a given situation will be determined in accordance with preliminary pilot investigations on the specific containers to be tested.

It is also contemplated that, in an alternative embodiment, the testing system 10 could be integrated into a packaging assembly line, with container tests being conducted at regular intervals during the production process. In this type of situation, the support structure 12 and platform member 14 as illustrated in FIG. 1 would either not be necessary or would need to be modified to enable integration of these components into the production line.

Positioned on the planar upper surface 16 of the platform member 14 associated with the support structure 12 is a selected test container 18. In a preferred embodiment, the container 18 includes a side wall portion 20 with an interior region 22 surrounded by the side wall portion 20. The interior region 22 is partially or entirely occupied by a selected filling material 24. If the interior region 22 is only partially occupied with the filling material 24, the remainder of the interior region 22 may be placed under a vacuum. Alternatively, the unoccupied portion of the interior region 22 can be supplied with air or other gaseous/liquid compositions. Many different container types, filling materials, and internal environments may be employed in the present invention which shall not be limited in this regard. For example, the container 18 can be made from metal (e.g. stainless steel, aluminum, tin, or copper), glass, a paper composition such as cardboard, plastic (e.g. styrene, polyethylene terephthalate, or polyvinyl chloride), and combinations of these materials. The filling material may involve many different compositions including food products, edible liquid materials, medicines, and chemicals in dry or liquid form. Exemplary food products will consist of fruits, vegetables, and meats, with representative liquid materials involving dairy products, edible oils, water, and beverages. The size of the container 18 may also vary, depending on its intended purpose. Accordingly, the present invention shall not be limited regarding the size of the container 18 to be tested. The system 10 may be configured to test containers having a capacity of a few ounces to thousands of pounds.

While the invention is especially useful in testing cans, bottles, and other food/beverage packages, it is likewise prospectively useful in many other areas. For example, the claimed system may have military applications, and can be used to analyze munitions and other weapon materials for explosive quantity and fill characteristics as discussed above. The claimed system can therefore be used to analyze many different types of containers and filling materials (both solids and liquids) in a wide variety of technical fields.

To analyze the fill characteristics of the test container 18, the testing system 10 further includes sound generating means 30 (schematically illustrated in FIG. 1) for producing sound waves and delivering the sound waves to the container 18 as discussed below. In particular, the sound generating means 30 will consist of audio signal production means 32 for producing an initial audio signal. The sound generating means 30 will further include amplifier means 34 connected to the audio signal production means 32 for generating an amplified audio signal from the initial audio signal, and at least one speaker unit 36 operatively connected to the amplifier means 34. The speaker unit 36 is designed to receive the amplified audio signal and generate sound waves from the audio signal for application to the container 18 in a controlled manner. The sound waves will cause vibration of the container 18 as discussed below. Many different commercially available components may be used as the sound generating means 30, audio signal production means 32, amplifier means 34, and speaker unit 36. Accordingly, the present invention shall not be limited to the use of any specific components in connection with the items listed above. In an exemplary and preferred embodiment, the audio signal production means 32 will consist of a white noise generator capable of producing sound (white noise) at a preferred frequency range of 100–5000 Hz. The term "white noise" as used herein shall involve noise or sound waves having a constant energy per unit bandwidth at each frequency in the selected frequency range. The use of white noise in the system 10 is preferred because it provides a rapid and simplified audio response for obtaining highly accurate results in connection with a variety of different containers. An exemplary white noise generator suitable for use as the audio signal production means 32 will consist of a digital or analog circuit which supplies constant energy per unit bandwidth. An exemplary and preferred system having the foregoing characteristics which is suitable for use as the sound generating means 30 (e.g. the audio signal production means 32) is commercially available from Neel Electronics, Inc. of Laguana Niguna, Calif. (USA)—product no. SCAN100. However, other sound generating systems which may be used as the audio signal production means 32 include a general purpose digital noise generator commercially available from the Atlas/Soundolier Co. of Fenton, Mo. (USA)—model no. GPN-1200; and a noise generator unit available from the Wavetek Co. of San Diego, Calif. (USA) —model no. 132-S-725. Accordingly, the present invention shall not be limited to any particular systems in connection with the audio signal production means 32 and the other components of the sound generating means 30 as stated above.

The amplifier means 34 (which is operatively and electrically connected to the audio signal production means 32) may likewise involve any amplifier system known in the art which is able to produce a sound output sufficient to cause vibration of the container 18 during a test procedure. An exemplary and preferred apparatus suitable for this purpose will consist of a 5–60 watt power amplifier with low distortion, high common mode rejection, and a typical gain bandwidth product of 10 MHz. A representative system which is suitable for use as the amplifier means 34 is commercially available from Neel Electronics, Inc. of Laguana Niguna, Calif. (USA)—product no. SCAN100. This commercial product also incorporates the preferred audio signal production means 32 therein as previously indicated. The amplifier means 34 is used to generate an amplified audio signal from the initial audio signal produced by the audio signal production means 32.

Finally, the amplifier means 34 is operatively and electrically connected to the speaker unit 36 which is schematically illustrated in FIG. 1. The speaker unit 36 is used to deliver the amplified audio signal (in the form of sound waves) to the test container 18. As discussed below, the preferred volume level associated with the sound waves delivered by the speaker unit 36 will be about 70–80 decibels in accordance with the embodiment described herein, although this parameter can be varied as determined by preliminary pilot studies. The selected speaker unit 36 may involve many different types, sizes, and configurations, with the present invention not being limited to any particular speaker system. For example, conventional magnetic loudspeaker units having a diameter of about 1–10 inches may be employed. It is likewise desired that the selected speaker unit be capable of operating in a frequency range of about 100–5000 Hz. An exemplary and preferred loudspeaker having these characteristics which is suitable for use as the speaker unit 36 is commercially available from Radio Shack, Inc. (The Tandy Corp.) of Fort Worth, Tex. (USA) —product no. 40-1022B. This particular loudspeaker has a diameter of 4 inches, and smooth frequency response from 50 Hz to 7000 Hz. As stated above, many different speaker systems can be used as the speaker unit 36, with the size and configuration of the desired loudspeaker depending on the particular container 18 to be tested. In addition, as discussed below in the section entitled "Operation", it is preferred in the present embodiment that the speaker unit 36 be positioned at a distance $D_1$ (FIG. 1) of about 2–4 inches from the container 18. In the situations described herein, this distance will provide an optimal degree of testing accuracy, although different distances may be used depending on the size of the container 18, the testing environment, the frequency and volume of the sound waves being applied, and other factors. Accordingly, the selected distance $D_1$ between the speaker unit 36 and the container 18 will again be determined by preliminary pilot tests.

The testing system 10 further includes vibration sensing means 50 for detecting vibration of the container 18 during the application of sound waves to the container 18 by the sound generating means 30. As schematically shown in FIG. 1 the vibration sensing means 50 preferably includes laser light delivery means 52 for applying a reference beam of laser light to the container 18 during the application of sound waves to the container 18. More specific information regarding the characteristics of the reference beam of laser light will be provided below. As the reference beam comes in contact with the exterior surface 54 of the container 18, it is reflected off of the container 18 to generate a reflected beam of laser light. As discussed in the section entitled "Operation", the reflected beam will experience a Doppler shift in frequency compared with the reference beam. The term "Doppler shift" as used herein basically involves the amount of change in the observed frequency of a wave due to the Doppler effect. The "Doppler effect" generally involves a change in the observed frequency of a wave caused by relative motion of the source and observer. In the present case, the Doppler shift of the container 18 during a test procedure relates to the vibrational speed of the container 18 (e.g. radial/line-of-sight movement). The Doppler shift of the reflected beam is caused by vibration of the container 18, with the amount of Doppler shift being dependent on the amount of vibration (e.g. the vibrational frequency and amplitude) experienced by the container 18. In turn, the specific amount of vibration experienced by the container 18 will depend in a unique and characteristic manner on the fill characteristics of the container 18 as they relate to (1) the amount and type of filling material 24 within the interior region 22 of the container 18; and/or (2) the presence or absence of a vacuum within the container 18. The fill characteristics of the container 18 will influence and control vibration of the container 18 because the system 10 measures the fundamental modes of vibration which, in turn, are affected by container mass/dimensions, fill material (e.g. fill characteristics as defined above), and the like. By comparing the Doppler shift associated with the test container 18 and a standardized reference (control) container having known fill characteristics, it can be determined whether the test container 18 is properly filled and/or has the desired degree of structural integrity as indicated above. Any differences in the vibration profiles/signatures of the test container and the reference container will indicate that the test container deviates in some manner from the desired fill characteristics associated with the production process of interest. The test container can then be physically (manually) inspected to determine if it has the wrong filling materials therein, the incorrect amount of filling materials, and/or the presence of leaks.

Finally, the vibration sensing means 50 will include frequency shift detector means 56 which is used to track, measure, and characterize the Doppler shift of the reflected beam of laser light during a test procedure. The frequency shift detector means 56 provides quantitative information which is ultimately used to make a comparative analysis of the container 18 and its fill characteristics relative to standardized reference data.

The present invention shall not be limited to any specific components in connection with the vibration sensing means 50 and its particular sub-systems (e.g. the laser light delivery means 52 and the frequency shift detector means 56). In this regard, a number of different systems may be used for this purpose. In an exemplary and preferred embodiment, the vibration sensing means 50 will consist of a commercially-available laser vibrometer apparatus. Laser vibrometers are capable of accurately detecting characterizing, and measuring the vibration of a test object by measuring the Doppler shift (defined above) of reflected laser light from a vibrating object. In particular, Doppler shift values are determined by comparing the reflected beam to the reference beam as previously discussed using optical heterodyning approaches. A representative laser vibrometer system suitable for use in the testing system 10 as the vibration sensing means 50 is commercially available from Dantec Electronics Inc. of Allendale, N.J. (USA)—model number 41X60. This system uses a vibrometer head having optical beam-focusing elements therein (part no. 41X61) in combination with a laser adaptor kit (part no. 41X66), a beam diameter adaptor (part no. 60X26), and a fiber manipulator (part no. 60X24). The vibrometer head is fiber-optically coupled to a laser light source which, in the Dantec 41X60 system will consist of a 10 mW He-Ne coaxial laser (part no. 9138A6024). The vibrometer head and the laser light source collectively comprise the laser light delivery means 52 associated with the vibration sensing means 50 as discussed above.

From a functional standpoint, the laser light generated by the laser light source in the Dantec system enters the vibrometer head where a beam splitter divides the beam into a first beam component and a second beam component. The second beam component passes through a retarder plate and a plurality of lenses. Thereafter, it strikes the vibrating object and is reflected as indicated above so that it reenters the vibrometer head. The reflected beam then passes through another retarder plate and into a Bragg cell (e.g. an acoustooptic modulator which ultrasonically varies the amplitude or phase of a light beam). As a result, the reflected beam undergoes a 90° polarization shift. The reflected beam and the first component of the initial beam are then combined, followed by a 45° polarization adjustment using internal optics within the vibrometer head. The combined beam is thereafter separated into two additional beam components, again using internal optics within the vibrometer head. The two additional beam components are ultimately directed into two photosensors which produce signals that are sent to a mixer which generates an electrical output. The electrical output is sent to a frequency tracker unit (Dantec part no. 55N20) which functions as the frequency shift detector means 56. The Doppler frequency data delivered to the tracker unit specifically involves a linear characterization of the vibrational movement of the test object. The tracker unit produces output voltage values which correspond to the vibrational movement of the test object. The output voltage values may then be further manipulated and statistically treated in order to compare the vibrational characteristics of the test container 18 to standardized data from a reference (control) container as previously discussed. As a result, the test container 18 can be analyzed to determine if it has the proper fill characteristics. Further information regarding the treatment of output voltage values received from the vibration sensing means 50 (e.g. the laser vibrometer and tracker unit described above) will be provided in the "Operation" section presented below.

As indicated above, the model 41X60 laser vibrometer coupled with the model 55N20 tracker unit produced by Dantec Electronics Inc. represents an exemplary and preferred vibration sensing means 50 which incorporates the laser light delivery means 52 and frequency shift detector means 56 in a highly efficient manner. In particular, the foregoing system is characterized by the following specifications: (1) vibration amplitude range=$10^{-8}$ m–1 m; (2) vibration frequency range=DC to 0.74 MHz (VCO output); (3) vibration velocity range=$10^{-6}$ m/s–3 m/s; (4) vibration acceleration range=$10^{-11}$ m/s$^2$–0.3×$10^6$ m/s$^2$; (5) response time=1 ls; (6) analog output with 100 ohm source using the model 55N20 tracker=1–10 V, DC to 27 kHz; and (7)

dynamic range=>160 dB. Further information regarding the parameters listed above, the operational characteristics of the Dantec system, and laser vibrometer technology in general is provided in a report entitled "Fibre Vibrometer", *Dantec Technical News* (May 1988) by Dantec Electronics Inc. and in a document entitled "41X62 Compact Laser Vibrometer—manual" pp. 13–14, Ch. 5 (Sept. 1991) produced by Dantec Electronics Inc., both of which are incorporated herein by reference.

As previously indicated, the present invention shall not be limited to the specific laser vibrometer system listed above. Other commercially-available laser vibrometers may likewise be used with an equal degree of effectiveness. Additional representative laser vibrometers which may be used as the vibration sensing means 50 in the manner described above are available from the following sources: (A) Polytec, Inc. of Costa Mesa, Calif. (USA)—model OFV-1002; (B) Ometron, Inc. of Sterling, Va. (USA)—model 1940; (C) MTI Instruments of Latham, N.Y. (USA)—model MTI 2000; and (D) Optech, Inc. of Herndon, Va. (USA)—model DMM-1a.

Regarding the effective distance between the test container 18 and the laser light delivery means 52 associated with the vibration sensing means 50, the precise distance will vary in view of numerous parameters including the size and type of the container 18 as determined by preliminary experimental testing. However, in a preferred embodiment which is generally suitable for the containers and testing conditions set forth herein, the effective distance $D_2$ (FIG. 1) between the container 18 and the laser light delivery means 52 (e.g. the vibrometer head) will be about 2–36 inches. It should also be noted that the vibration sensing means 50 (including the laser light delivery means 52) may be placed at any position relative to the container 18 (e.g. to the side of the container 18 or at a position directly opposite the sound generating means 30 so that the container 18 is positioned between the vibration sensing means 50 and the sound generating means 30 as illustrated in FIG. 1).

Operation

As indicated above, the testing system 10 can be used in a rapid and efficient manner to analyze the fill characteristics of a test container 18. The resulting data can then be compared with standardized reference data. To accomplish this goal, the sound generating means 30 is used to apply sound waves to the container 18 so that vibration of the container 18 occurs. The density, viscosity, quantity, and elastic properties of the filling material 24 within the interior region 22 of the container 18 (as well as the presence or absence of a vacuum therein) affect the frequencies at which vibration resonances occur and likewise influence the amplitudes of the resonances. The vibration sensing means 50 (e.g. a selected laser vibrometer as previously discussed) is then used to apply a reference beam of laser light to the vibrating container 18. The reference beam strikes the container and is reflected to produce a reflected beam of laser light which undergoes a Doppler frequency shift as indicated above. The resulting Doppler frequency shift information obtained from the frequency shift detector means 56 can thereafter be used in a comparative manner to determine if the fill characteristics of the container 18 meet desired standards.

With particular reference to FIG. 1, a more detailed discussion of the testing system 10 and claimed testing methods will now be provided. To test the container 18 (which rests on the platform member 14 associated with the support structure 12), the sound generating means 30 is oriented so that the speaker unit 36 is positioned at the desired distance $D_1$ from the container 18. Thereafter, the sound generating means 30 is activated in order to apply sound waves (schematically shown in FIG. 1 at reference number 60) to the container 18. The sound waves 60 are generated by the audio signal production means 32, amplifier means 34, and speaker unit 36 which cooperate as described above. The duration and frequency of the sound waves 60 applied to the container 18 will vary in accordance with a variety of factors including the type and size of the test container 18. The exact parameters associated with the sound waves 60 will be determined in a given situation by preliminary investigations on the containers of interest. However, in a preferred embodiment which is suitable for the general purposes described herein, the sound waves 60 will be applied at a frequency of about 100–5000 Hz over a time period of about 0.01–10 seconds at a volume of about 70–80 decibels (dB). As noted above, a preferred distance $D_1$ between the speaker unit 36 and the container 18 will be about 2–4 inches, although this value can likewise be varied in accordance with routine experimentation.

The application of sound waves 60 to the container 18 will result in vibration of the container 18 at a particular frequency and amplitude which depend on the density, viscosity, quantity, and elastic properties of the filling material 24 within the container 18, as well as the presence or absence of a vacuum therein. Accordingly, the amount of vibration experienced by the container 18 (e.g. the amplitude and frequency of the vibration) can be used to create a vibration profile or signature (discussed below) of the container 18 to determine whether it is properly filled and/or has the desired degree of structural integrity.

During the application of sound waves 60 to the container 18, the laser light delivery means 52 associated with the vibration sensing means 50 is activated in order to apply a reference beam 62 of laser light to the container 18 (with reference beam 62 being enlarged for the sake of clarity in FIG. 1). The specific characteristics of the reference beam 62 will vary in view of the testing environment and the type of container 18 being analyzed as determined by preliminary investigations. However, in a preferred embodiment which is suitable for the purposes set forth herein, the reference beam 62 will be applied to the container 18 at a power level of about 0.5–5 mW. The precise power level for a given situation within the foregoing range will depend on a variety of factors including the distance $D_2$ (FIG. 1) between the container 18 and the laser light delivery means 52 (vibrometer head) as discussed above, and the reflective characteristics of the exterior surface 54 associated with the container 18. If the surface 54 is highly reflective, then a reduced-intensity reference beam 62 would be appropriate. In a preferred embodiment, the reference beam 62 will have a beam diameter of about 0.4–5 mm, which again can be varied within the foregoing range in accordance with the other testing conditions being employed. Likewise, in the embodiment described herein, the effective distance $D_2$ between the container 18 and the laser light delivery means 52 (e.g. the vibrometer head) will be about 2–36 inches which is also subject to change in accordance with variations in testing conditions. It should also be noted that the reference beam 62 may be applied to any position on the container 18, provided that the selected position will allow the beam 62 to be reflected as discussed below. Also, to ensure that accurate results are achieved, the beam 62 should be applied at the same position on both the test container 18 and the reference container of interest.

During operation of the laser light delivery means 52, the reference beam 62 comes in contact with the container 18 and is immediately reflected from the container 18 to generate a reflected beam 70 of laser light (enlarged for the sake of clarity in FIG. 1). As discussed above, the reflected beam 70 undergoes a Doppler shift in frequency compared with the reference beam 62, with the Doppler shift being caused by vibration of the container 18. The amount of the Doppler shift experienced by the reflected beam 70 is again dependent on the amount of vibration (e.g. the vibrational frequency and amplitude) associated with the container 18. The fill characteristics of the container 18 will influence and control vibration of the container 18 for the reasons listed above.

The laser light delivery means 52 associated with the vibration sensing means 50 is specifically oriented relative to the container 18 so that the reflected beam 70 re-enters the vibration sensing means 50 (e.g. the vibrometer head used in the above-described laser vibrometer). The reflected beam 70 will thereafter undergo standard optical adjustment and polarization steps within the laser vibrometer as previously discussed. Finally, the reflected beam 70 is analyzed using the frequency shift detector means 56 (e.g. the previously-described tracker unit) in order to measure the Doppler shift experienced by the reflected beam 70. Operation of the tracker unit is discussed above. As a result, an output voltage in analog form is obtained from the frequency shift detector means 56 which is directly proportional to the amount of vibration experienced by the test container 18. This step allows the test container 18 to be quantitatively characterized in a unique and accurate manner. The output of the frequency shift detector means 56 (which basically involves the amount of Doppler shift associated with the reflected beam 70) can thereafter be compared with previously-determined Doppler shift data obtained from a reference (control) container having known fill characteristics. To ensure accurate and complete results, test data involving the control container will be obtained in the same manner described above regarding the test container 18, and will involve the same testing parameters. Any differences in test data between the test container 18 and the reference container will indicate that the container 18 does not have the correct filling material 24 therein, contains an improper amount of filling material 24, and/or has a leak in the side wall portion 20 of the container 18 which allows air or other contaminants into the container 18. The test container 18 can then be manually inspected (e.g. opened) as part of an accurate and rapid quality control program to determine why it deviated from the control container. If no deviations exist between the test container 18 and the reference container, opening or further activity associated with the test container 18 is not needed.

Data Treatment and Interpretation

Figure 2:
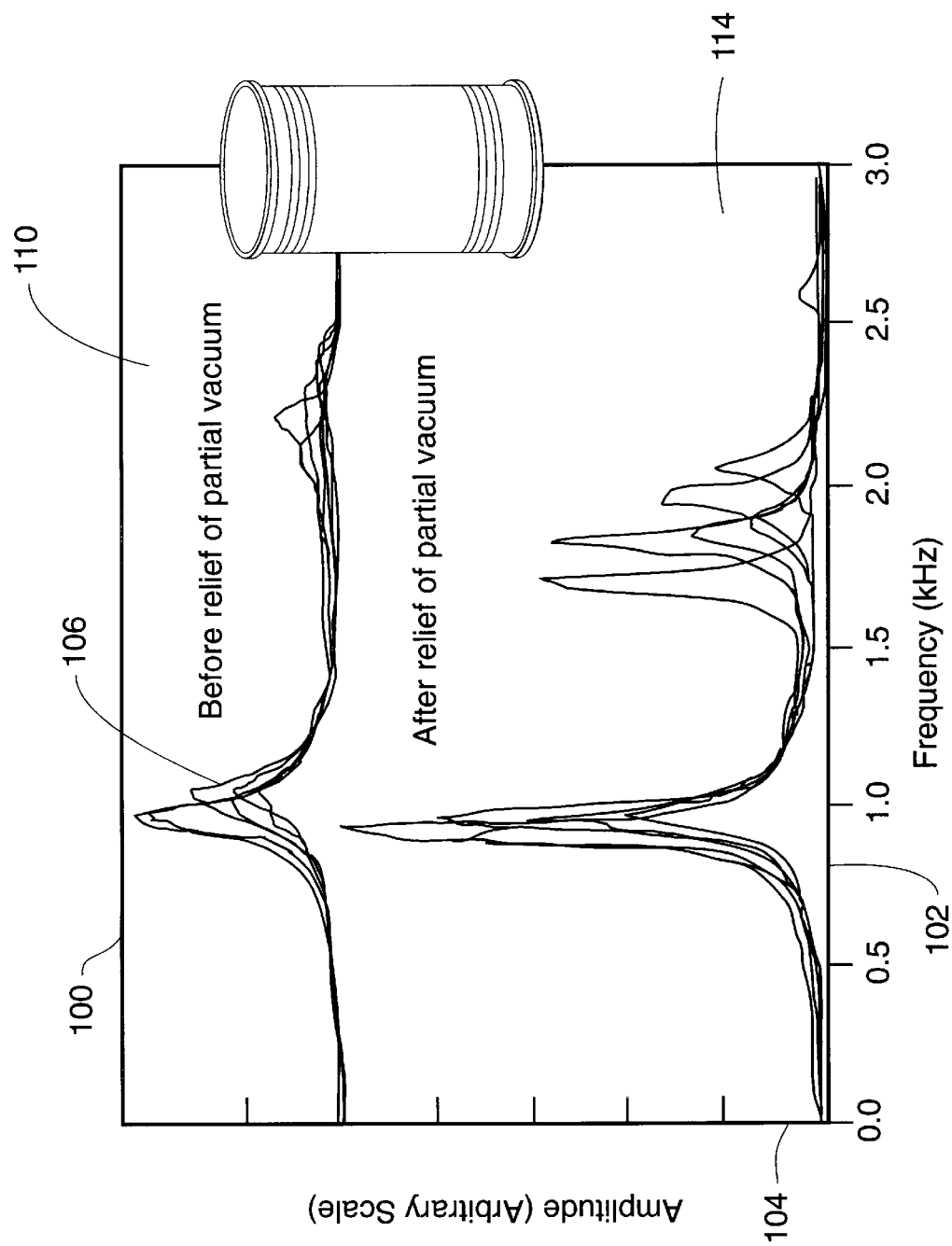
FIG. 2 is a comparative vibration profile of a representative test container (e.g. a metal can) produced in accordance with a first Example involving the method of the present invention.
Figure 3:
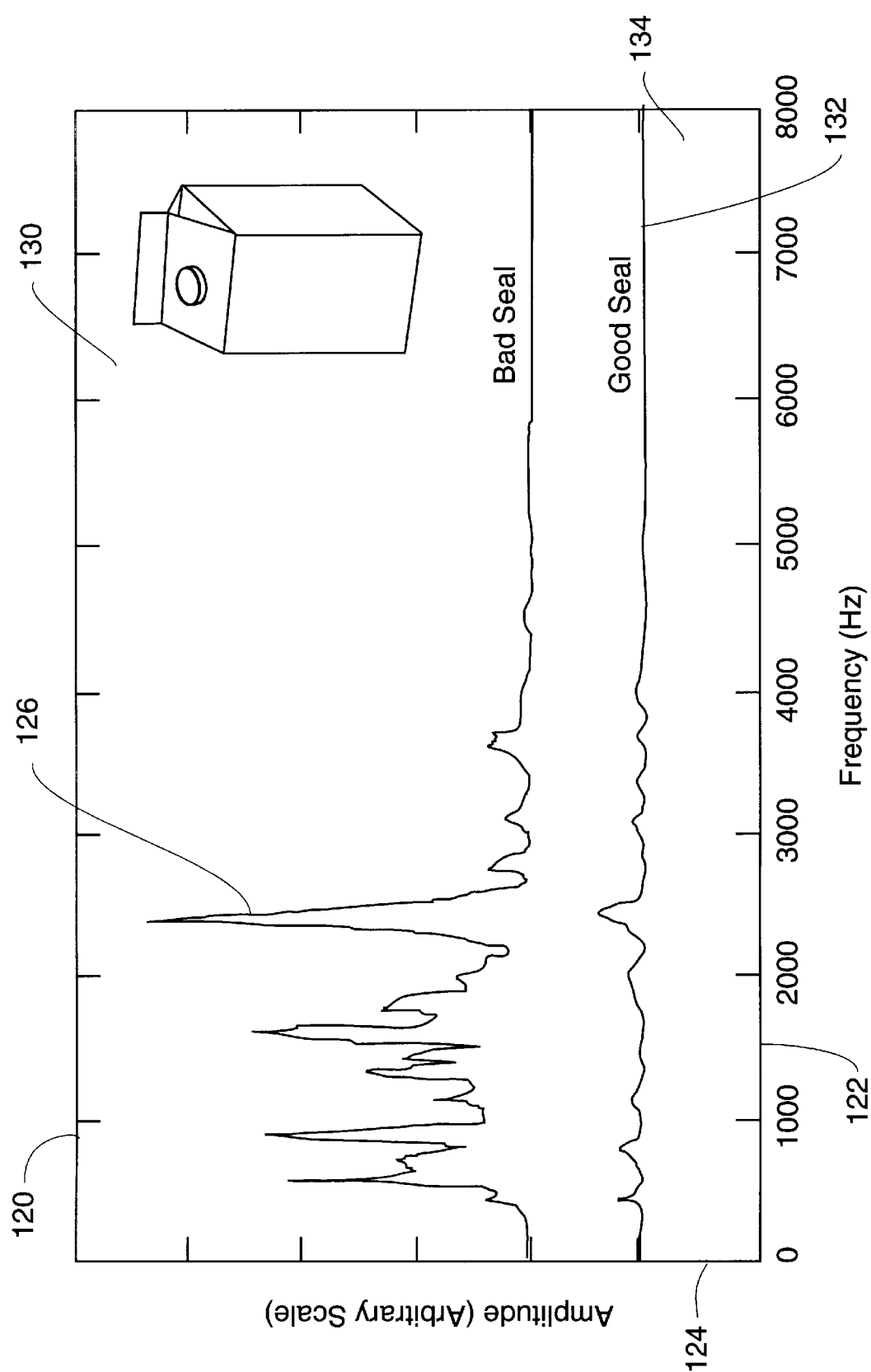
FIG. 3 is a comparative vibration profile of a representative test container (e.g. a cardboard carton) produced in accordance with a second Example.

If desired, the information obtained from the testing system 10 as described above can be further manipulated, treated, and statistically interpreted using many different approaches. Accordingly, the present invention shall not be limited to any particular data treatment or analysis method. Of particular interest is an approach in which the Doppler shift of the reflected beam 70 of laser light is measured multiple times during the application of sound waves 60 to the container 18 (e.g. about 2–100 times in a preferred embodiment). As a result, a set of data values is produced which can thereafter be used to generate an averaged vibration profile of the container 18 based on the multiple data values. This type of sampling method which involves multiple data values that are averaged together to produce a vibration signature (e.g. frequency v. amplitude) corresponding to the container 18 is highly detailed and accurate. The averaged vibration profile associated with the container 18 can then be compared with a previously-determined averaged vibration profile of a reference (control) container having known fill characteristics. Representative vibration profiles for numerous containers are illustrated in FIGS. 2–4 and described in the Examples presented below.

To implement this data treatment method, analog voltage data from the frequency shift detector means 56 (e.g. the tracker unit) is converted to digital form using conventional analog-to-digital conversion techniques which are well known in the art. Prior to conversion, the analog data is electronically filtered to prevent aliasing. "Aliasing" involves the generation of spurious signals at lower frequencies which reduces the accuracy of the data acquisition process. In accordance with standard digital analysis techniques, the accurate reproduction of a frequency requires sampling at twice the designated frequency (conventionally known as the Nyquist frequency). If frequencies greater than the Nyquist frequency are present, aliasing occurs. To prevent aliasing, the analog data is treated using a conventional low pass filter prior to digitization which is set at one-half the sampling rate (e.g. a 5 KHz filter for a 10 KHz sampling rate). The term "low pass filter" as used herein involves a filter system in which frequency components above the threshold value associated with the filter system are rejected.

Analysis of the resulting data to produce an averaged vibration profile of the container 18 (also characterized in an equivalent manner as a "reference signature" or "spectra") involves a number of statistical calculations. An exemplary and preferred statistical analysis package which is suitable for use in this embodiment of the invention is commercially available from SAS Institute Inc. of Cary, N.C. (USA) under the name "SAS". Statistical analysis of the data is conducted using data processing means 78 which basically involves a conventional computer system 80 illustrated schematically in FIG. 1 (e.g. a DOS-based IBM 386—33 MHz PC). However, other computer systems may be used for this purpose, with the present invention not being limited to any specific computer unit. As discussed below, the data processing means 78 is specifically used to generate a vibration profile (signature) of the container 18 based on the Doppler shift of the reflected beam 70 of laser light. With reference to FIG. 1, the data processing means 78 is operatively connected to the vibration sensing means 50 (e.g. the frequency shift detector means 56).

Regarding statistical analysis of the data, an averaged vibration profile for a given container is obtained by first taking the multiple digital data points derived from the repeated measurements described above and averaging fast Fourier transforms (FFTs). For a given function f(t), a Fourier transform involves the function F(x) which is equal to $1/\sqrt{2X}$ times the integral over t from $-\infty$ to $\infty$ of f(t)exp (itx). A fast Fourier transform is defined as a Fourier transform which uses the Cooley-Tukey algorithm to reduce the number of required operations. An exemplary and representative vibration profile is obtained by averaging 100 FFTs. Each FFT is typically computed from 8192 data points, collected at a sampling rate of 83.3 kHz. Classification of an inspected object is accomplished by statistical processing of the frequency spectrum. The preferred statistical approach (which involves the foregoing statistical package or other comparable methods) uses a nonparametric "k nearest neighbor" method where the value of k is typically 3. The desired comparisons between the test data and standardized reference data as discussed above can then be obtained based on the "proximity" of the spectrum associated with the test data to the spectrum involving the reference data.

The input to the classification algorithm is a set of frequency and amplitude pairs. Each pair consists of frequency and amplitude values which relate to the largest resonance peak in a specific frequency range associated with the calculated spectrum. In an exemplary and preferred embodiment, 16 non-overlapping frequency ranges will be used, resulting in a total of 32 parameters characterizing each spectrum. Each set of 32 parameters defines a point in parameter space which is assigned to a class based upon the class membership of its three nearest neighbors. If two of the three nearest neighbors belong to the same class, then the unknown item will be assigned to that class. The determination of "proximity" is based on the Mahalanobis distance between the points in accordance with the following equation:

$$d(x,y) = \sqrt{(x-y)'V^{-1}(x-y)} \qquad (1)$$

[wherein x and y are observation vectors]
The Mahalanobis distance is similar to the Euclidean distance, except that it is "adjusted" based on the intercorrelations of the variables in the study. The Mahalanobis distance to a point of a known class will be smaller if the point belongs to a broadly scattered class of points than if it belongs to a tightly grouped class of points. Further general information regarding the foregoing statistical approach (including equation (1) and the variables listed above) is presented in the SAS/STAT User's Guide, Version 6, 4th ed., Vol. 1, Ch. 20 (pp. 678–685), SAS Institute, Inc., Cary, N.C. (USA) which is incorporated herein by reference. Likewise, exemplary vibration profiles (e.g. spectra) are graphically illustrated in FIGS. 2–4 and described in the Examples presented below.

Using the foregoing statistical approach, a typical data acquisition process would involve a number of steps incorporating the basic procedures listed above. For example, the following steps would be used to analyze a test container 18: (1) activate the sound generating means 30; (2) using the vibration sensing means 50 (e.g. the laser vibrometer), compute a frequency spectrum by averaging 100 FFTs computed from 2048 data points sampled at a rate of 83.3 kHz, with sampling being initiated and controlled by the selected data processing means 78 (e.g. the computer system 80); (3) write the resulting frequency spectrum to the computer system 80; (4) with the sound generating means 30 still in operation, compute a second frequency spectrum using the computer system 80 by averaging 100 FFTs; (5) write the second frequency spectrum to the computer system 80; (6) deactivate the sound generating means 30; (7) using the computer system 80, generate a third frequency spectrum (with the sound generating means 30 not operating); (8) repeat step (7) to produce a fourth frequency spectrum; (9) average the first and second spectra together (which were obtained during operation of the sound generating means 30); (10) average the third and fourth spectra together (which were obtained after deactivation of the sound generating means 30); (11) subtract the average of the third and fourth spectra from the average of the first and second spectra; and (12) write the difference from the subtraction in step (11) to the computer system 80. The resulting information is then processed by the computer system 80 in accordance with the statistical approaches described above (e.g. using the previously described SAS analysis package) to generate vibration profiles/spectra of the type shown in FIGS. 2–4 (discussed below).

As stated above, many different analytical procedures and computer systems may be used to produce frequency spectra for test containers in accordance with the invention. In this regard, the basic concepts of the claimed invention are not exclusively dependent on any particular data treatment methods or statistical approaches, with the foregoing information being provided for example purposes. To illustrate the production of representative frequency profiles/spectra using the testing system 10, the following Examples are provided:

EXAMPLE 1

In this Example, vibration profiles were made regarding a group of six vacuum-sealed cans containing a food product (e.g. canned sweet peas), followed by further testing of the cans to obtain additional vibration profiles after they were punctured to allow air into the cans. The specific components and equipment listed above in connection with the sound generating means 30, the vibration sensing means 50, and the computer system 80 were employed. For example, a model 41×60 laser vibrometer system produced by Dantec Electronics Inc. was used in combination with a model 55N20 tracker unit also produced by Dantec Electronics Inc. Likewise, the sound generating means 30 and associated components produced by Neel Electronics, Inc. as discussed above were used in all of the tests. In addition, the tests involved the following parameters:

1. Sound frequency=200–20,000 Hz.
2. Sound volume level=80 dB.
3. Sound duration=10 seconds.
4. Number of frequency shift measurements made during sound application=100.
5. Distance $D_1$ (FIG. 1) between the speaker unit of the sound generating means and each container (can)=4 inches.
6. Energy level associated with the reference laser beam=2.5 mW.
7. Reference laser beam diameter=0.48 mm.
8. Type of can being tested=type 303×406 steel construction.
9. Number of cans tested=6.
10. Contents of each can (amount and type)=10.25 oz. of sweet peas and 6.75 oz. of liquid (primarily water).
11. Position on each can where laser light was applied=on the top of the can at the center.

As stated above, identical testing procedures were used for both the punctured and unpunctured cans. The test cans were each punctured at the top to avoid liquid leakage. Using the statistical and data treatment methods listed above, vibration profiles (e.g. vibration spectra) were produced for the six vacuum sealed cans and the same cans after they were punctured. These spectra are graphically illustrated in FIG. 2. Specifically, the spectral graph 100 shown in FIG. 2 involves vibration frequency in Hz (x-axis 102) v. vibration amplitude using an arbitrary scale (y-axis 104). Spectrum 106 in the upper portion 110 of the graph 100 actually involves a composite display of the six initial vacuum-sealed cans superimposed over each other. Spectrum 112 in the lower portion 114 of the graph 100 involves a composite plot of the six cans after being punctured.

As shown in spectrum 112, the resonance peaks for the punctured cans have larger amplitudes, are sharper, and are shifted downward in frequency compared with spectrum 106 involving the unpunctured cans. Accordingly, the vibrational characteristics of the sealed cans are significantly different from those of the punctured cans as indicated by the different profiles shown in FIG. 2. This Example clearly demonstrates the value of the present invention in quality control processes associated with perishable packaged foods (e.g. vacuum-sealed food products). Using the approaches described above, food product containers can be tested for leaks in a rapid and effective manner which is important from both a safety and efficiency standpoint.

EXAMPLE 2

In this Example, vibration profiles were made using cardboard containers filled with a liquid beverage composition. One container was properly sealed to avoid leakage, while the other container was partially opened to produce a leak. Vibration profiles (e.g. spectra) were then made for each container. The specific components and equipment listed above in connection with the sound generating means 30, the vibration sensing means 50, and the computer system 80 were again employed as previously discussed in Example 1. In addition, the tests associated with this Example involved the following parameters:
1. Sound frequency=20–20,000 Hz.
2. Sound volume level=80 dB.
3. Sound duration=10 seconds.
4. Number of frequency shift measurements made during sound application=100.
5. Distance $D_1$ (FIG. 1) between the speaker unit of the sound generating means and each container=12 inches.
6. Energy level associated with the reference laser beam=2.5 mW.
7. Reference laser beam diameter=0.48 mm.
8. Type of container being tested=cardboard.
9. Number of containers tested=2 (one sealed container and one leaky container).
10. Contents of each container=iced tea.
11. Position on each container where reference beam of laser light was applied=on the side at the middle of each container.

Both the sealed container and the leaky container were tested using the same methods and procedures. Vibration profiles (e.g. vibration spectra) were produced for the sealed container and the leaky container using the statistical approaches and data treatment methods described above. These spectra are graphically illustrated in FIG. 3. Specifically, the spectral graph 120 shown in FIG. 3 involves the vibration frequency of each container in Hz (x-axis 122) v. vibration amplitude using an arbitrary scale (y-axis 124). Spectrum 126 in the upper portion 130 of the graph 120 corresponds to the leaky container, while spectrum 132 in the lower portion 134 of the graph 120 involves the sealed container.

As indicated in FIG. 3, the spectrum 126 corresponding to the leaky container is significantly different from the spectrum 132 associated with the sealed container. Specifically, the spectra 126, 132 shown in FIG. 3 involve different frequencies and amplitudes. This Example demonstrates the usefulness of the present invention in quality control processes involving the packaging of food products in non-metal containers. In accordance with the invention, leakage in non-metal food product containers can be detected with a high degree of accuracy using a non-invasive approach.

EXAMPLE 3

In this Example, vibration profiles were made using an empty plastic (polyethylene terephthalate) beverage bottle pressurized with air at different levels. The test bottle was initially pressurized with air at a level of 10 psi and thereafter pressurized with air at 12 psi. Vibration spectra were generated for the bottle at each pressure level. The specific components and equipment listed above in connection with the sound generating means 30, the vibration sensing means 50, and the computer system 80 were again employed as previously discussed in Example 1. In addition, the tests associated with this Example involved the following parameters:
1. Sound frequency=20–20,000 Hz.
2. Sound volume level=80 dB.
3. Sound duration=10 seconds.
4. Number of frequency shift measurements made during sound application=100.
5. Distance $D_1$ (FIG. 1) between the speaker unit of the sound generating means and the test bottle=12 inches.
6. Energy level associated with the reference laser beam=2.5 mW.
7. Reference laser beam diameter=0.48 mm.
8. Type of bottle being tested (e.g. size, construction materials, and wall thickness)=1.0 liter polyethylene terephthalate with a wall thickness involving 2.0 mils.
9. Number of bottles tested=1 (two tests were conducted with the same bottle—one test at 10 psi of air, and another test at 12 psi of air).
10. Position on the bottle during each test where the reference beam of laser light was applied=side of the bottle at the middle.

Both of the tests in this Example were conducted using the same methods and procedures. Vibration profiles (e.g. vibration spectra) were produced for the bottle at 10 psi and 12 psi using the statistical approaches and data treatment methods described above. These spectra are graphically illustrated in FIG. 4. Specifically, the spectral graph 150 shown in FIG. 4 involves the vibration frequency of the test bottle in Hz (x-axis 152) v. vibration amplitude using an arbitrary scale (y-axis 154). Spectrum 156 in the upper portion 160 of the graph 150 involves the bottle at 12 psi, while spectrum 162 in the lower portion 164 of the graph 150 involves the bottle at 10 psi.

As shown in FIG. 4, the spectrum 156 for the bottle at 12 psi is different from the spectrum 162 associated with the bottle at 10 psi. The spectrum 156 involving the bottle at higher pressure levels is characterized by a frequency shift and differences in amplitude compared with spectrum 162. These differences are apparently caused by increased stiffness of the bottle at higher pressure levels. This Example demonstrates the usefulness of the claimed invention in quality control situations where container pressure levels are an important factor. Accordingly, the detection of abnormal pressure levels within a container can be undertaken in a rapid and non-invasive manner.

The present invention represents an advance in the art of container testing and provides many benefits. These benefits include: (1) the ability to test containers in a non-destructive, non-intrusive manner which is highly accurate and economically efficient; (2) the capability of the present invention to accomplish container testing in a rapid manner using a minimal amount of equipment; and (3) the provision of a testing system which is especially suitable for both mass production manufacturing processes and the on-demand testing of individual samples. Having herein described preferred embodiments of the invention, it is anticipated that suitable modifications may be made thereto by individuals skilled in the relevant art which nonetheless remain within the scope of the invention. In this regard, the present invention shall only be construed in accordance with the following claims:

I claim:

1. A method for determining the fill characteristics of a container comprising the steps of:

providing a container comprising a side wall and an interior region therein surrounded by said side wall, said side wall further comprising an exterior surface and said interior region comprising a filling material therein;

providing sound generating means for generating and delivering sound waves to said container, said sound generating means comprising at least one speaker unit;

positioning said at least one speaker unit of said sound generating means about 2–4 inches from said container;

activating said sound generating means in order to apply said sound waves to said exterior surface of said side wall of said container from said at least one speaker unit without opening said container, said sound waves being applied over a time period of about 0.01–10 seconds at a frequency of about 100–5000 Hz and a volume level of about 70–80 decibels, said sound waves causing said container to vibrate;

applying a reference beam of laser light to said exterior surface of said side wall of said container without opening said container during application of said sound waves to said container, said reference beam being applied to said exterior surface of said side wall of said container at a power level of about 0.5–5 mW with a beam diameter of about 0.4–5 mm, said reference beam coming in contact with said exterior surface of said side wall of said container and being reflected therefrom to generate a reflected beam of laser light, said reflected beam undergoing a Doppler shift in frequency compared with said reference beam, said Doppler shift being caused by vibration of said container;

measuring said Doppler shift of said reflected beam of laser light; and comparing said Doppler shift of said reflected beam of laser light to previously-determined Doppler shift data obtained from a reference container having known fill characteristics.

* * * * *